US012754046B2

(12) United States Patent
Kaushik et al.

(10) Patent No.: US 12,754,046 B2
(45) Date of Patent: Oct. 6, 2026

(54) MICRO-VIBRATION TESTING DEVICE FOR VITAL PARAMETER EVALUATION AND A METHOD THEREOF

(71) Applicant: Turtle Shell Technologies Private Limited, Bengaluru (IN)

(72) Inventors: Pavan Kumar Kaushik, Bangalore (IN); Pooja Kadambi, Bangalore (IN); Gaurav Parchani, Bangalore (IN)

( * ) Notice: Subject to any disclaimer, the term of this patent is extended or adjusted under 35 U.S.C. 154(b) by 281 days.

(21) Appl. No.: 18/391,329

(22) Filed: Dec. 20, 2023

(65) Prior Publication Data

US 2024/0210221 A1 Jun. 27, 2024

(30) Foreign Application Priority Data

Dec. 22, 2022 (IN) ............................ 202241074717

(51) Int. Cl.
*G01D 18/00* (2006.01)
*A61B 5/11* (2006.01)
(Continued)

(52) U.S. Cl.
CPC ............ *G01D 18/00* (2013.01); *A61B 5/1102* (2013.01); *G01D 3/022* (2013.01); *G01D 3/08* (2013.01); *G01P 21/00* (2013.01); *G01V 13/00* (2013.01)

(58) Field of Classification Search
CPC .......... G01D 18/00; G01D 3/022; G01D 3/08; A61B 5/1102; G01P 21/00; G01V 13/00
(Continued)

(56) References Cited

U.S. PATENT DOCUMENTS 6,254,551 B1 * 7/2001 Varis ........................ A61B 5/11 600/595
7,846,104 B2 * 12/2010 MacQuarrie ........... A61B 5/349 600/501
(Continued)

FOREIGN PATENT DOCUMENTS

CA 2875901 A1 * 12/2012 ......... A61B 5/14552
CA 3150852 A1 * 2/2021 ............. G16H 15/00
(Continued)

OTHER PUBLICATIONS

Candan Caner et al., The Programmable ECG Simulator, DOI 10.1007/s10916-008-9140-1, J Med Syst (2008) 32:355-359 (Year: 2008).*

*Primary Examiner* — Christopher E Mahoney
*Assistant Examiner* — Kevin C Butler
(74) *Attorney, Agent, or Firm* — SLEMAN & LUND LLP

(57) ABSTRACT

The present invention discloses a micro-vibration testing device for vital parameter evaluation and a method thereof. The system (100) comprises at least one user device (102), at least one vital monitor (104), and at least one ballistic micro-vibration validation device (106). The ballistic micro-vibration validation device (106) comprises a heart module (202), and a microcontroller module (204) wherein the heart module (202) comprises a vibration module (302) and the microcontroller module (304) comprises a MOSFET Relay (304). The vibration module (302) in the heart module (202) simulates the mechanical micro-vibrations of a heart beat wherein the micro-vibrations are controlled by the micro-controller module (204) which drives the vibration module (302) using the MOSFET relay (304). The system (100) enables a wide range of cardiac states to be simulated, from a healthy heart beat to arrhythmias.

6 Claims, 6 Drawing Sheets

(51) Int. Cl.

| | |
|---|---|
| ***G01D 3/02*** | (2006.01) |
| ***G01D 3/08*** | (2006.01) |
| ***G01P 21/00*** | (2006.01) |
| ***G01V 13/00*** | (2006.01) |

(58) Field of Classification Search
USPC .......................................................... 73/1.01
See application file for complete search history.

(56) References Cited

U.S. PATENT DOCUMENTS

| | | | | |
|---|---|---|---|---|
| 8,364,250 | B2 * | 1/2013 | Moon | A61B 5/721 600/513 |
| 9,026,202 | B2 * | 5/2015 | Albert | A61B 5/349 600/513 |
| 11,510,624 | B2 * | 11/2022 | Grassere | A61B 5/6838 |
| 11,751,772 | B2 * | 9/2023 | Parchani | G16H 50/30 600/526 |
| 2002/0109595 | A1 * | 8/2002 | Cairo | A61B 5/0006 340/539.12 |
| 2006/0122517 | A1 * | 6/2006 | Banet | A61B 5/6816 600/323 |
| 2008/0114220 | A1 * | 5/2008 | Banet | A61B 5/14551 600/382 |
| 2010/0298651 | A1 * | 11/2010 | Moon | A61B 5/0285 600/595 |
| 2011/0066009 | A1 * | 3/2011 | Moon | A61B 5/743 600/509 |
| 2011/0066044 | A1 * | 3/2011 | Moon | A61B 5/318 600/485 |
| 2011/0066045 | A1 * | 3/2011 | Moon | A61B 5/021 600/485 |
| 2011/0066050 | A1 * | 3/2011 | Moon | A61B 5/0205 600/509 |
| 2012/0288840 | A1 * | 11/2012 | Gurdin | G09B 23/34 434/272 |
| 2013/0196301 | A1 * | 8/2013 | Carson | G09B 23/281 434/268 |
| 2014/0350362 | A1 * | 11/2014 | Raptis | A61B 5/0015 600/300 |
| 2015/0211944 | A1 * | 7/2015 | Yarden | G01K 13/20 600/300 |
| 2016/0027345 | A1 * | 1/2016 | Carson | G09B 23/32 434/262 |
| 2016/0111023 | A1 * | 4/2016 | Pybus | G09B 23/303 434/268 |
| 2016/0317048 | A1 * | 11/2016 | Chan | A61B 5/6833 |
| 2017/0027521 | A1 * | 2/2017 | Geva | A61B 5/6815 |
| 2017/0135585 | A1 * | 5/2017 | Liu | A61B 5/7282 |
| 2018/0132735 | A1 * | 5/2018 | Weebadde | A61B 5/0006 |
| 2019/0295398 | A1 * | 9/2019 | Khac | A61B 5/02438 |
| 2021/0127983 | A1 * | 5/2021 | Parchani | A61B 5/6892 |
| 2024/0161923 | A1 * | 5/2024 | Lane | G16H 40/67 |
| 2025/0168318 | A1 * | 5/2025 | Marty | H04N 17/004 |

FOREIGN PATENT DOCUMENTS

| | | | | | |
|---|---|---|---|---|---|
| CN | 102123656 | A | * | 7/2011 | G16H 40/67 |
| CN | 106859683 | A | | 6/2017 | |
| CN | 110603575 | B | * | 8/2022 | G09B 23/306 |
| CN | 120052843 | A | * | 5/2025 | A61B 5/681 |
| CN | 120093262 | B | * | 9/2025 | G01S 13/88 |
| FR | 2867595 | A3 | * | 9/2005 | G09B 23/32 |
| KR | 102600954 | B1 | * | 11/2023 | A61B 5/086 |
| WO | WO-2018126254 | A1 | * | 7/2018 | G09B 23/32 |
| WO | WO-2021030499 | A1 | * | 2/2021 | A61B 5/6817 |
| WO | WO-2022135712 | A1 | * | 6/2022 | A61B 5/02141 |
| WO | WO-2025056965 | A1 | * | 3/2025 | G16H 50/20 |

* cited by examiner

MICRO-VIBRATION TESTING DEVICE FOR VITAL PARAMETER EVALUATION AND A METHOD THEREOF

FIELD OF INVENTION

The field of invention generally relates to a micro-vibration validation testing. More specifically, it relates to a system and method for a micro-vibration validation for vital parameter evaluation.

BACKGROUND

The quantitative evaluation of an individual's health status requires the measurement of physiological parameters. The monitoring of vitals can provide important physiological insights for medical diagnosis and well-being management, making it useful for health monitoring. The vital signs monitoring techniques include optical-based, radar-based, WiFi-based, RFID-based, and acoustic-based methods.

The vital signs monitoring techniques must be validated against a gold-standard reference across a representative patient sample and under representative conditions to gain clinical acceptance.

Typically, the most commonly used method for validating vitals monitors is to use an ECG simulator. However, ECG signals are unsuitable for validating vital monitors that use Ballisto Cardio Graphy (BCG) or Seismography (SG) because they simulate electrical activity rather than the ballistic micro-vibrations required by BCG-based vitals monitors.

Currently, existing systems can simulate micro-vibrations. However, they are mostly used for research purposes and unsuitable for testing vitals monitors. These technologies include shaker tables, pneumatic vibrators, and electrodynamic shakers.

Other existing systems have tried to address this problem. However, their scope was limited to the technologies that are bulky, expensive, and difficult to use. They are also not able to accurately simulate the wide range of cardiac conditions. Other systems also introduce noise vibrations that impact the testing.

Furthermore, the existing systems that are used to validate BCG monitors involve human subjects to artificially increase or decrease their vital parameters. Such an approach not only presents considerable risk to the human subject, but also fails to provide stable signals over a wide range of values.

Thus, in light of the above discussion, it is implied that there is a need for a system and method for a ballistic micro-vibration validation for vital parameters like breathing, heart rate, cardiac output etc. which is reliable and does not suffer from the problems discussed above.

OBJECT OF INVENTION

The principal object of this invention is to provide a system and method for a ballistic micro-vibration validation.

Another object of the invention is to provide a system and method to validate the vitals monitors.

A further object of the invention is to provide a system and method that can generate micro-vibrations for long durations without putting a human subject at risk, making it a more cost-effective option for monitor validation.

Another object of the invention is to generate micro-vibrations of various heart rates and durations, allowing it to be used to validate a variety of different monitors.

BRIEF DESCRIPTION OF FIGURES

This invention is illustrated in the accompanying drawings, throughout which, like reference letters, indicate corresponding parts in the various figures.

The embodiments herein will be better understood from the following description with reference to the drawings, in which.

STATEMENT OF INVENTION

The present invention discloses a ballistic micro-vibration validation system for vitals monitor evaluation and a method thereof.

The system comprises at least one user device, at least one vital monitor, at least one ballistic micro-vibration validation device and a communication network.

The ballistic micro-vibration validation device is a versatile and reliable tool for testing vitals monitors and other cardiac devices.

The ballistic micro-vibration validation device comprises a heart module, and a microcontroller module. The heart module comprises a vibration module and the microcontroller module comprises a MOSFET Relay.

The vibration module in the heart module simulates the mechanical micro-vibrations of a heartbeat. The micro-vibrations are controlled by the microcontroller module which drives the vibration module using the MOSFET relay. The system enables a wide range of cardiac states to be simulated, from a healthy heartbeat to arrhythmias.

DETAILED DESCRIPTION

The embodiments herein and the various features and advantageous details thereof are explained more fully with reference to the non-limiting embodiments that are illustrated in the accompanying drawings and/or detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The present invention discloses a ballistic micro-vibration validation system for a vital monitor. The ballistic micro-vibration system can validate the vital monitor. The ballistic micro-vibration validation system can produce micro-vibrations that are more similar to the natural variability of the human heartbeat. Further, the ballistic micro-vibration validation system can simulate a wide range of micro-vibrations of various heart rates for long durations with high fidelity without putting a human subject at risk, making it a more cost-effective option for monitor validation.

Figure 1:
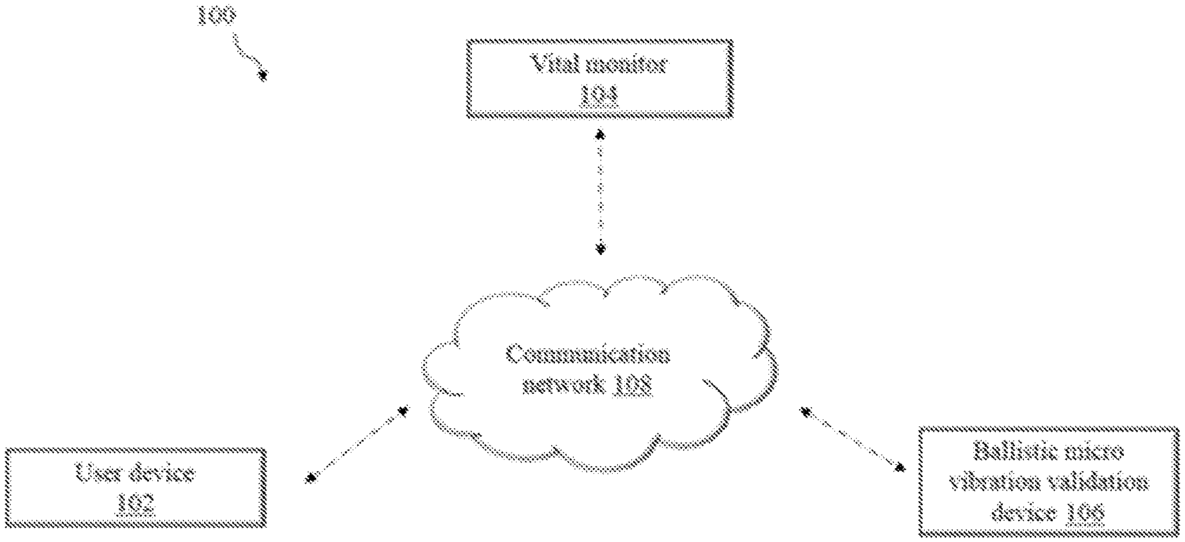
FIG. 1 depicts/illustrates a block diagram of a system for ballistic micro-vibration validation of vitals monitor, in accordance with an embodiment of the present disclosure.

FIG. 1 depicts/illustrates a block diagram of a system for ballistic micro-vibration validation of a vital monitor, in accordance with an embodiment of the present disclosure.

The system 100 comprises at least one user device 102, at least one vital monitor 104, at least one ballistic micro-vibration validation device 106 and a communication network 108.

In an embodiment, the at least one user device 102 may comprise one or more of wearable device, mobile phones, PDA, smartphones, smart band, smart watch, laptop, computer, etc. The user device 102 may have a user application which can control the operations of the system 100.

The at least one vital monitor 104 is configured to evaluate at least one vital sign of at least one patient. The vital sign may comprise at least one of heart rate, blood oxygen saturation, and blood pressure among others. The at least one vital monitor 104 is validated without putting a human subject at risk.

The at least one ballistic micro-vibration validation device 106 is configured to generate at least one micro-vibrations of at least one of various heart rates and durations, enabling it to be used to validate the at least one vital monitor 104.

The at least one vital monitor 104 comprises one or more sensors for measuring at least one of heart rate, blood oxygen saturation, and blood pressure.

Typically, the at least one ballistic micro-vibration validation device 106 is connected to the at least one vital monitor 104 and the at least one user device 102 via the communication network 108. One skilled in the art may recognize that the communication network 108 may be a wired network or wireless network.

Furthermore, the wired communication may be carried out by any one of the network configurations such as LAN, WAN, etc. and the wireless communication may be carried out through Mobile Service Provider (MSP) and Internet Service Provider (ISP) having internet connection provided by an ISP provider, 2G/3G/4G/5G internet connection provided by the mobile service provider. The standard protocols such as TCP/IP, HTTP, FTP, UDP, IPV4, IPV6 etc. as known in the art, may be used for the wireless communication.

Figure 2:
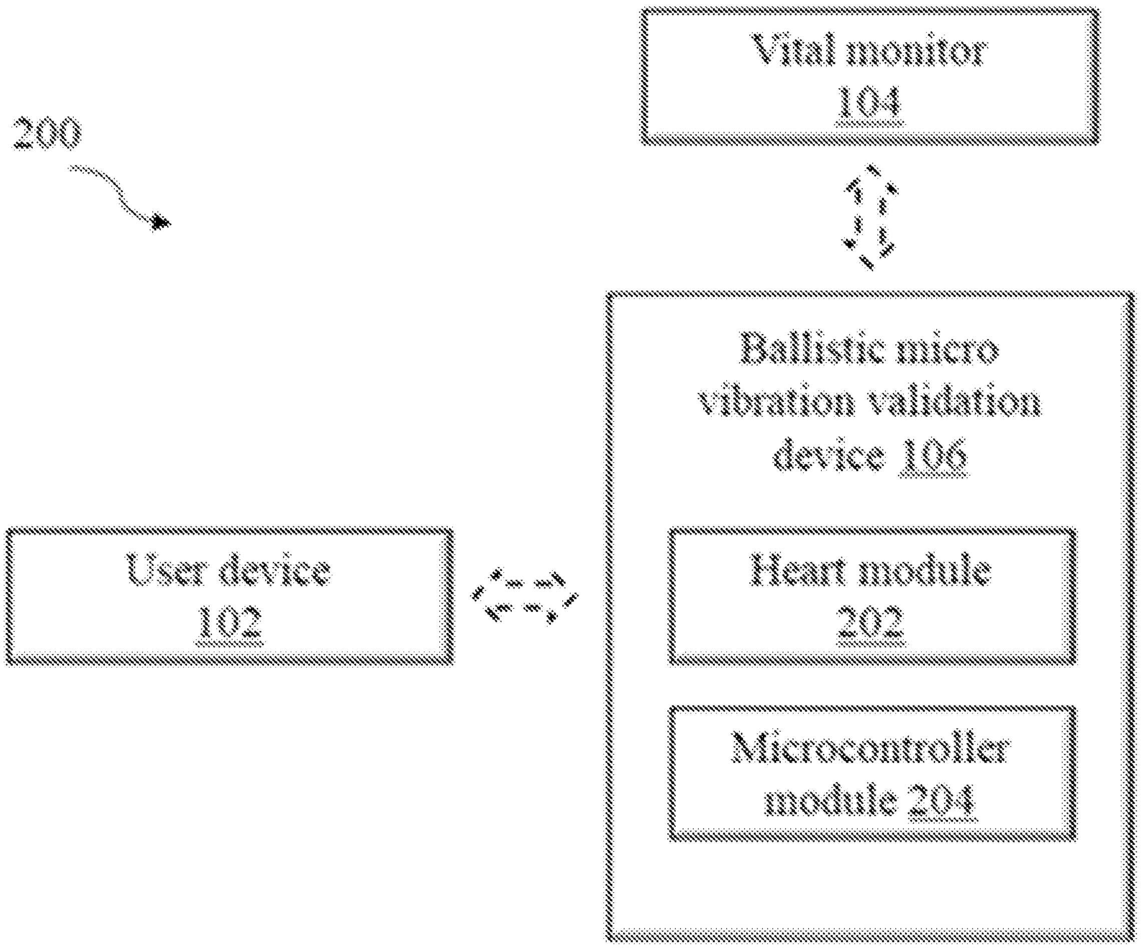
FIG. 2 depicts/illustrates a detailed block diagram of components of the system for ballistic micro-vibration validation of vitals monitor, in accordance with an embodiment of the present disclosure.

FIG. 2 depicts/illustrates a detailed block diagram of components of the system for ballistic micro-vibration validation of vitals monitor, in accordance with an embodiment of the present disclosure.

The ballistic micro-vibration validation device 106 comprises a heart module 202, and a microcontroller module 204. The heart module 202 simulates a mechanical micro-vibration of a heartbeat.

In an embodiment, the heart module 202 simulates heart rates as low as 25 bpm to 200 bpm, a heart rate variability (HRV) of Oms to 200 ms, and arrhythmias such as supraventricular tachycardia, bradycardia etc.

The microcontroller module 204 is configured to precisely control and deliver the power to the heart module 202. The microcontroller module 204 can independently vary heart rate. Further, the microcontroller module 204 can sweep and hold through a huge range of cardiac function states for vital monitor validation and quality assurance.

Figure 3A:
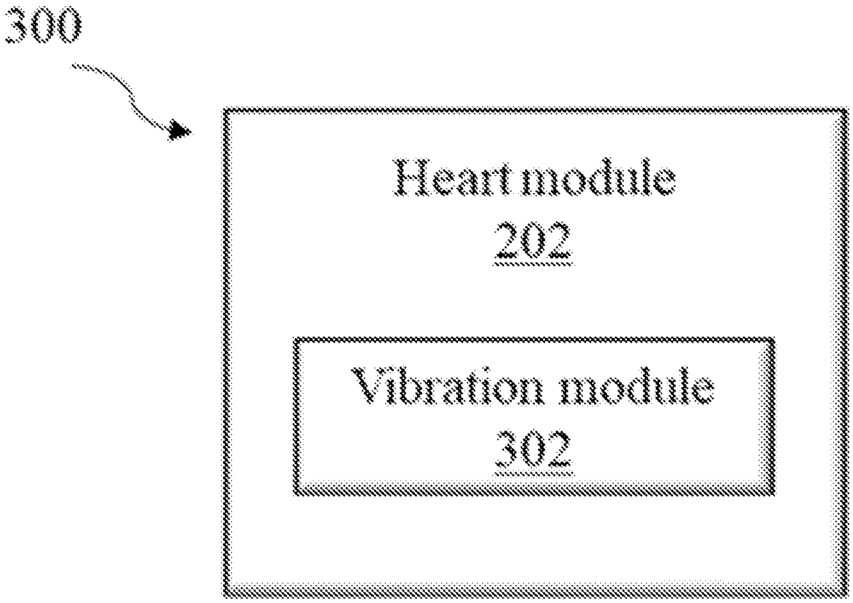
FIG. 3*a* depicts/illustrates a detailed block diagram of components of a heart module of ballistic micro-vibration validation system, in accordance with an embodiment of the present disclosure.

FIG. 3*a* depicts/illustrates a detailed block diagram of components of a heart module of a ballistic micro-vibration validation system, in accordance with an embodiment of the present disclosure.

In an embodiment, the cardiac cycle (lub-dub) comprises all of the physiological events associated with a single heartbeat. The atria and ventricles alternately contract in each cardiac cycle. Further, the cardiac cycle is split into two phases, systole that corresponds to the contraction phase and diastole that corresponds to the relaxation phase. Therefore, the cardiac cycle includes four stages comprising atrial systole, ventricular systole, atrial diastole, and ventricular diastole.

In an embodiment, the lub represents ventricular systole and diastole whereas dub represents atrial systole and diastole.

Typically, heart sounds are created from blood flowing through the heart chambers as the cardiac valves open and close during the cardiac cycle. The present invention replicates the micro-vibrations of the heart.

The heart module 202 comprises a vibration module 302. In an embodiment, the vibration module 302 is an Eccentric Rotating Mass (ERM) which simulates the mechanical micro-vibrations of the heartbeat.

The vibration of the heart is simulated by precise manipulation of the power and timing to the vibration module 302. Two short pulses in rapid succession are used to create a lub-dub signal. The lub-dub signal is repeated for every cycle and the interval is set based on the desired heart rate by the microcontroller module 204. Further, the interval is varied based on the desired heart rate variability (HRV) and arrhythmia condition.

Figure 3B:
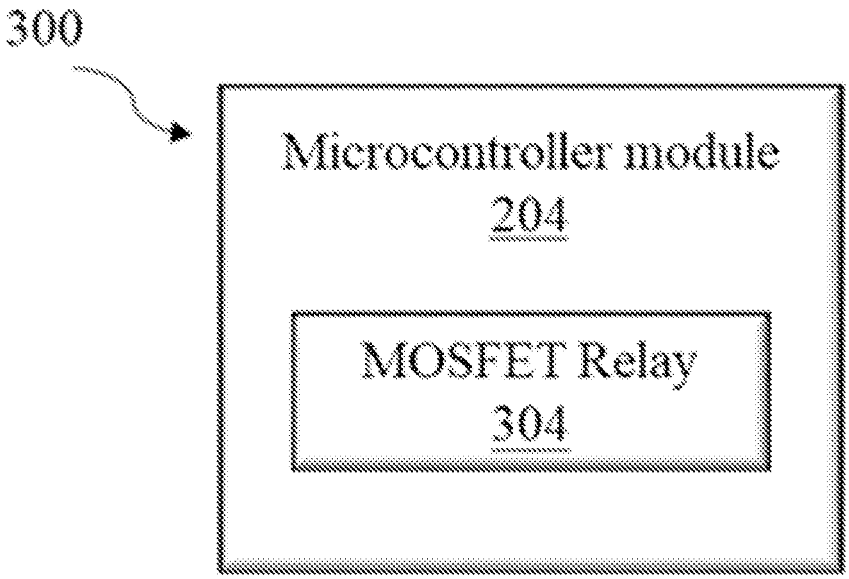
FIG. 3*b* depicts/illustrates a detailed block diagram of components of a microcontroller module of ballistic micro-vibration validation system, in accordance with an embodiment of the present disclosure.

FIG. 3*b* depicts/illustrates a detailed block diagram of components of a microcontroller module of ballistic micro-vibration validation system, in accordance with an embodiment of the present disclosure.

The microcontroller module 204 comprises a MOSFET Relay 304 which is configured to drive the ERM.

Figure 4:
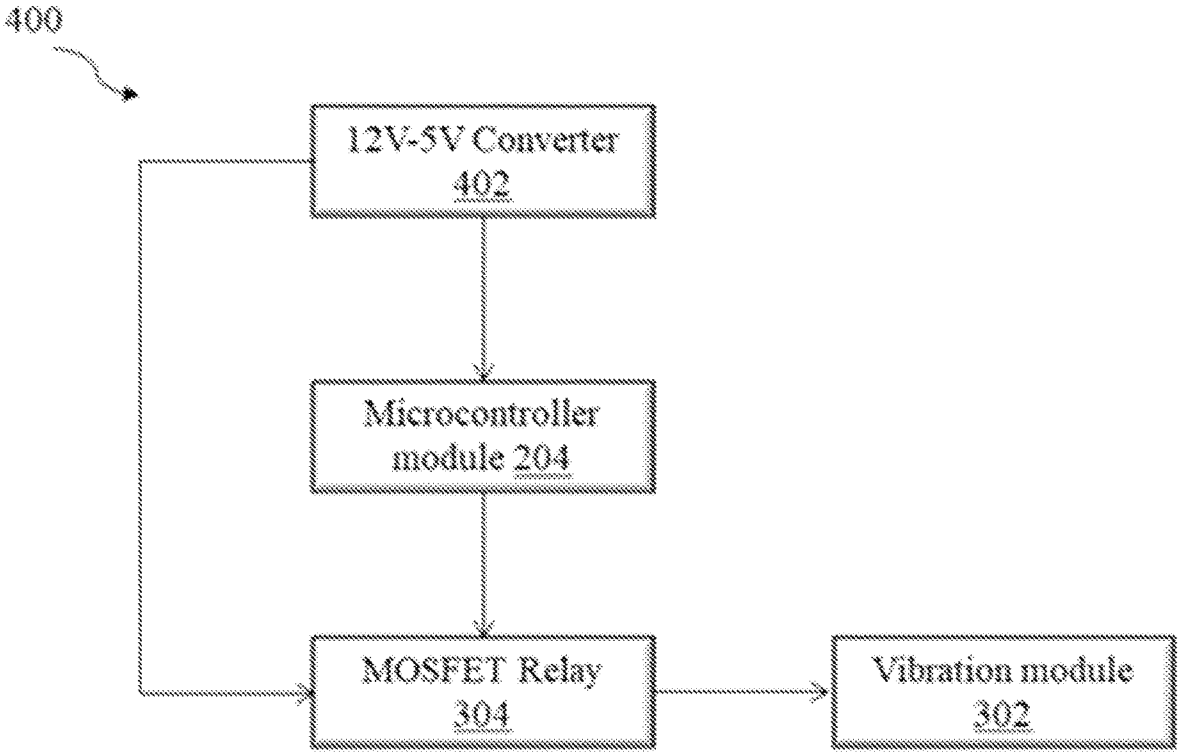
FIG. 4 depicts/illustrates a flow diagram of ballistic micro-vibration validation of vitals monitor, in accordance with an embodiment of the present disclosure.

FIG. 4 depicts/illustrates a flow diagram of ballistic micro-vibration validation of vitals monitor, in accordance with an embodiment of the present disclosure:

The flow diagram of ballistic micro-vibration validation of vitals monitor comprises a 12V-5V converter 402, a microcontroller module 204, a MOSFET Relay 304, and a vibration module 302.

The 12V-5V converter 402 is a step down converter which is configured to convert 12 V to 5V as the microcontroller module 204 require 5 V DC supply for its operation.

In an embodiment, the microcontroller module 204 comprises at least one of Arduino UNO, ESP32, and Rpi.

In the preferred embodiment, the microcontroller module 204 is an Arduino UNO. Arduino UNO is a low-cost, flexible, and easy-to-use programmable open-source microcontroller board.

In an embodiment, the MOSFET Relay 304 is an IRF 520 Relay. IRF520 MOSFET is a third-generation power MOSFET that provides fast switching, cost-effectiveness, strong design, and less resistance.

In an embodiment, the vibration module 302 is a vibration motor. With a high number of revolutions per minute, the motor is constantly being displaced and moved by these asymmetric forces, thereby creating micro-vibration by repeated displacement of the motor.

The ballistic micro-vibration validation system 100 is an electromechanical system. In an embodiment, the system 100 comprises the heart module 202 and the microcontroller module 204. The heart module 202 is configured to simulate the micro-vibrations of individual heart beats, whereas the microcontroller module 204 is configured to control at least one of duration and intensity of the micro-vibrations. These two modules work together to enable the system 100 to simulate a wide range of cardiac states, from a healthy heartbeat to arrhythmias. The generation of micro-vibrations of various heart rates and durations that closely match the natural variability of the human heartbeat, facilitates the system 100 to validate the at least one vital monitor 104.

Figure 5:
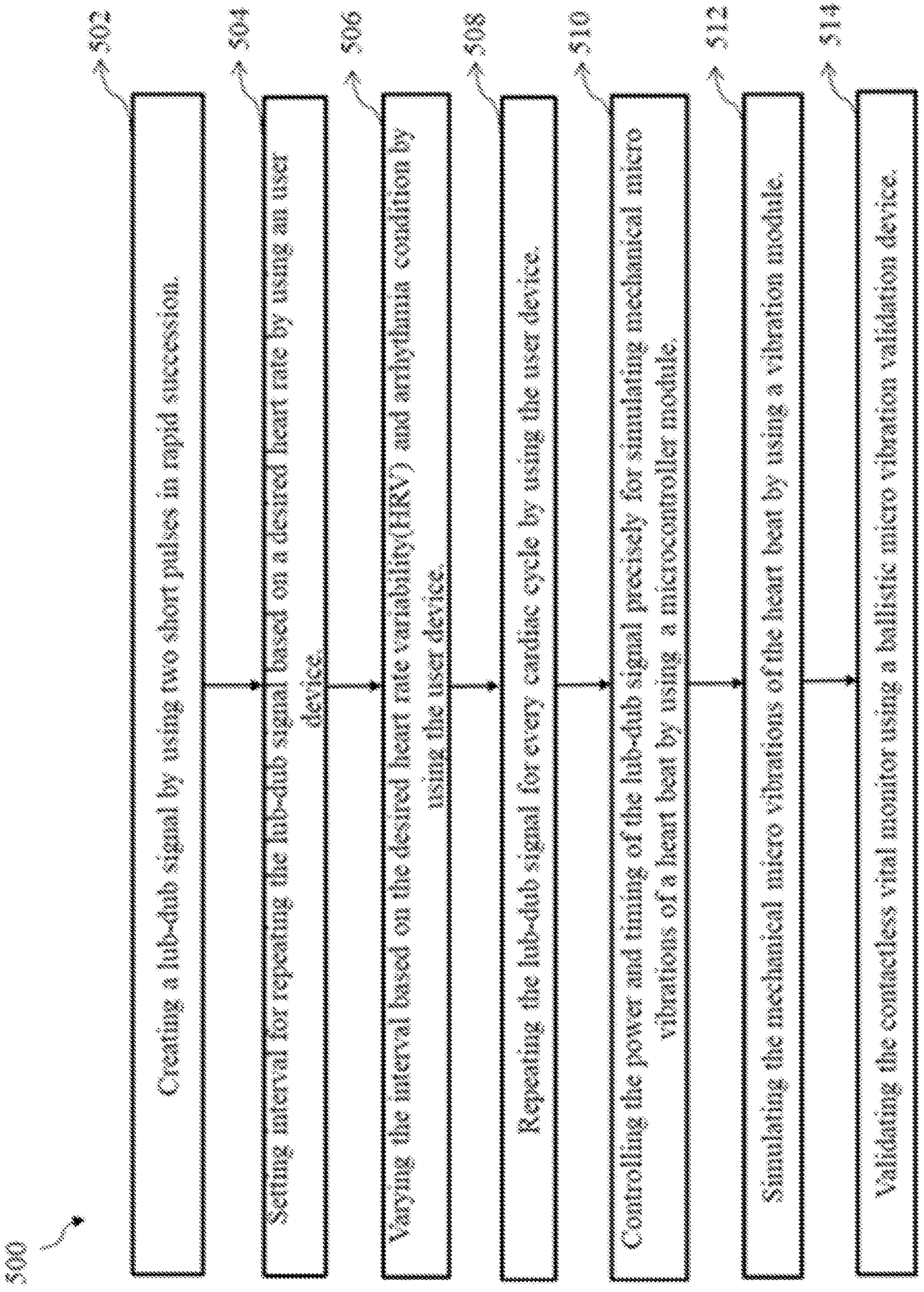
FIG. 5 illustrates a method for ballistic micro-vibration validation of vitals monitor evaluation, in accordance with an embodiment of the present disclosure.

FIG. 5 illustrates a method for ballistic micro-vibration validation of vitals monitor evaluation, in accordance with an embodiment of the present disclosure;

The method begins with creating a lub-dub signal by using two short pulses in rapid succession, as depicted at step 502. Subsequently, the method 500 discloses setting interval for repeating the lub-dub signal based on a desired heart rate by using a user device, as depicted at step 504. Thereafter, the method 500 discloses varying the interval based on the desired heart rate variability (HRV) and arrhythmia condition by using the user device, as depicted at step 506. Subsequently, the method 500 discloses repeating the lub-dub signal for every cardiac cycle by using the user device, as depicted at step 508.

Thereafter, the method 500 discloses controlling the power and timing of the lub-dub signal precisely for simulating mechanical micro-vibrations of a heart beat by using a microcontroller module, as depicted at step 510. Subsequently, the method 500 discloses simulating the mechanical micro-vibrations of the heart beat by using a vibration module, as depicted at step 512. Thereafter, the method 500 discloses validating the vital monitor using a ballistic micro-vibration validation device, as depicted at step 514.

Figure 6:
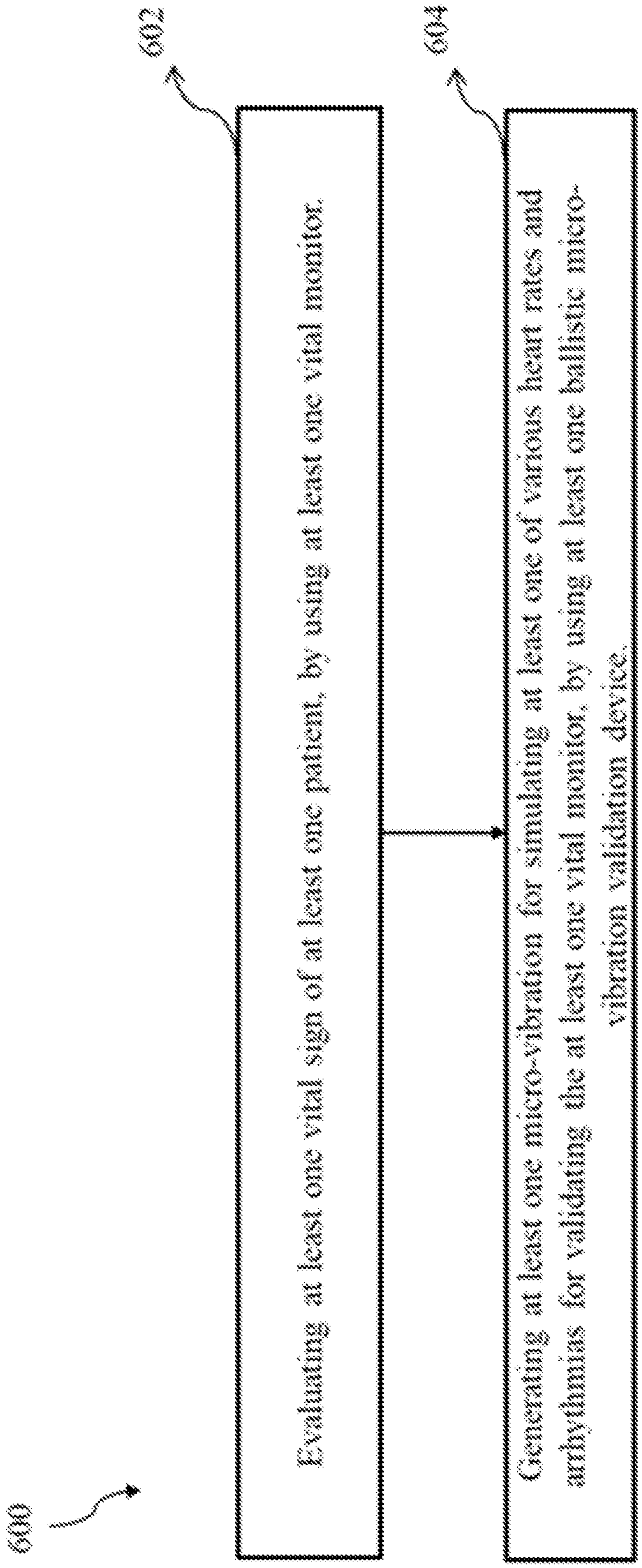
FIG. 6 illustrates a method for ballistic micro-vibration validation of vitals monitor, in accordance with an embodiment of the present disclosure.

FIG. 6 illustrates a method 600 ballistic micro-vibration validation of vitals monitor evaluation. The method 600 begins with evaluating at least one vital sign of at least one patient, by using at least one vital monitor, as depicted at step 602. Subsequently, the method 600 discloses generating at least one micro-vibration for simulating at least one of various heart rates and arrhythmias for validating the at least one vital monitor, by using at least one ballistic micro-vibration validation device, as depicted at step 604.

The advantages of the current invention include validation of the vital monitors.

An additional advantage is that the ballistic micro-vibration validation device can generate micro-vibrations for long durations without putting a human subject at risk, making it a more cost-effective option for monitor validation.

Furthermore, the ballistic micro-vibration validation system is more accurate than other validation systems, as it can reproduce the natural variability of the human heartbeat.

Applications of the current invention include medical device validation and micro-vibration validation.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the scope of the embodiments as described here.

We claim:

1. A system (100) for validating a micro-vibration based vitals monitor, comprising:

a ballistic micro-vibration validation device (106) configured to generate mechanical micro-vibrations for simulating heart rates and heart rate variabilities across a desired range for validating a vital monitor (104), wherein the ballistic micro-vibration validation device (106) comprises a heart module (202) comprising a vibration module (302) configured to simulate mechanical micro-vibrations of a heartbeat, wherein the vibration module (302) carries out the simulation by generating two short pulses in rapid succession; and a microcontroller module (204) configured to control duration and intensity of the two short pulses by;

delivering power to the vibration module (302);

setting an interval for repeating the two short pulses at a desired heart rate, and varying the interval based on a desired heart rate variability (HRV).

2. The system as claimed in claim 1, wherein the vibration module (302) is an Eccentric Rotating Mass (ERM) vibration motor to simulate a mechanical micro-vibrations.

3. The system (100) as claimed in claim 1, wherein the ballistic micro-vibration validation device (106) enables simulation of heart rates in a range from 25 beats per minute to 200 beats per minute, and a heart rate variability of up to 200 ms.

4. The system (100) as claimed in claim 1, wherein the operations of the vital monitor (104) and the ballistic micro-vibration validation device (106) is controlled by a user application in a user device (102).

5. The system (100) as claimed in claim 1, wherein the intensity and duration of the two short pulses generated by the vibration module (302) is controlled by the microcontroller module (204) via a user application in a user device (102).

6. The system (100) as claimed in claim 1, wherein the system (100) comprises a communication network (108) configured to connect a user device (102), the vital monitor (104), and the ballistic micro-vibration validation device (106).

* * * * *